United States Patent [19]

Yule

[11] Patent Number: 5,006,118

[45] Date of Patent: Apr. 9, 1991

[54] LIQUID TRANSFER ASSEMBLIES

[76] Inventor: Bruce Yule, 56, Grange Road, Saltwood, Hythe, Kent, England

[21] Appl. No.: 294,703

[22] Filed: Jan. 9, 1989

[30] Foreign Application Priority Data

Jan. 9, 1988 [GB] United Kingdom ................. 8800448

[51] Int. Cl.[5] ................................................ A61B 19/00

[52] U.S. Cl. .................................... 604/408; 604/247; 604/323; 128/DIG. 24; 383/44; 141/27

[58] Field of Search ........................ 604/403, 408–410, 604/411, 246, 247, 249, 256, 262, 323, 326, 905; 128/DIG. 24; 251/149.6, 149.7; 222/107; 383/43, 44, 53, 54, 906; 141/2, 25, 27, 313, 314

[56] References Cited

U.S. PATENT DOCUMENTS

| | | | |
|---|---|---|---|
| 1,534,913 | 4/1925 | Buck et al. | 137/322 |
| 3,570,484 | 3/1971 | Steer et al. | 604/249 |
| 3,610,297 | 10/1971 | Raaf | 141/27 |
| 3,806,086 | 4/1974 | Cloyd | 604/249 |
| 3,853,157 | 12/1974 | Madaio | 141/27 |
| 3,921,630 | 11/1975 | McPhee | 222/107 |
| 4,230,112 | 10/1980 | Smith . | |
| 4,443,219 | 4/1984 | Meisch et al. | 604/410 |
| 4,493,348 | 1/1984 | Lemmons . | |
| 4,553,970 | 11/1985 | Lewis, Jr. | 604/408 |
| 4,709,734 | 12/1987 | Rudick | 141/2 |
| 4,838,875 | 6/1989 | Somor | 604/408 |

FOREIGN PATENT DOCUMENTS

| | | | |
|---|---|---|---|
| 0156500 | 2/1985 | European Pat. Off. . | |
| 0158612 | 10/1985 | European Pat. Off. . | |
| 1413164 | 8/1965 | France . | |
| 2233245 | 10/1975 | France . | |
| 8607254 | 12/1986 | PCT Int'l Appl. | 604/408 |

*Primary Examiner*—Stephen C. Pellegrino
*Assistant Examiner*—Ralph A. Lewis
*Attorney, Agent, or Firm*—Pollock, Vande Sande & Priddy

[57] ABSTRACT

A liquid transfer assembly comprises a drug container and a syringe. The container has a bag of a flexible polymer with spines forming channels internally of the bag. The container is closed by a valve which has a valve member that is urged outwardly to a closed position by a helical spring. A luer taper bore in the valve is engaged by the nose of the syringe which, when inserted, depresses the valve member and opens the valve. Withdrawing the plunger of the syringe causes liquid drug in the bag to be sucked through the valve into the syringe and the bag to collapse about the remaining contents. The valve reseals the remaining contents on withdrawal of the syringe.

7 Claims, 2 Drawing Sheets

LIQUID TRANSFER ASSEMBLIES

BACKGROUND OF THE INVENTION

This invention relates to liquid transfer assemblies.

Previous methods of administering drugs to patients by means of a syringe involves fitting a needle to the syringe, breaking the neck off a glass drug ampoule, inserting the needle into the ampoule, drawing up the drug into the syringe and then injecting the drug in the usual way, after having evacuated air from the syringe.

There are many disadvantages with such methods which arise from the use of a glass ampoule to contain the drug.

For example, breaking the neck of the ampoule can result in glass shards being produced. These can in some case contaminate the contents of the ampoule and may be drawn up into the syringe. The shards and the broken parts of the ampoule also present a hazard to the clinician administering the drug by increasing the risk of cutting the skin and allowing contamination of or by the clinician. The act of inserting a sharply pointed needle into the narrow severed neck of the ampoule also presents the risk that the user will be pricked by the needle if it is not correctly inserted. Holding the drug ampoule and the syringe barrel while withdrawing the syringe plunger requires some manual dexterity and is difficult where the clinician's hands are wet or, in an emergency.

The glass ampoules require special disposal facilities after use, to avoid injury and contact with unused contents of the ampoules. Packaging and transport of the ampoules must be such that they will not be damaged. This can lead to bulky and expensive packaging.

The ampoules are only suitable for administration of a single dose, leading to wastage and complications where doses of different volumes need to be given. There is also the disadvantage that the drug must be transferred to the syringe immediately after having broken off the ampoule neck if the drug is of a kind that is affected by contact with air.

BRIEF SUMMARY OF THE INVENTION

It is an object of the present invention to provide an improved liquid container and a method of transferring liquid from such a container.

According to one aspect of the present invention there is provided a liquid transfer assembly, comprising a syringe and a liquid container, the liquid container comprising a reservoir with a flexible wall and an opening to the reservoir including a valve, the valve being urged to a normally closed position to prevent liquid leaving the container, the valve being openable by engagement with the syringe, the wall being adapted to collapse about the contents of the container as liquid is withdrawn by the syringe such that the internal volume of the container is maintained substantially equal to the volume of liquid in the container, and the internal surface of the wall being provided with a surface formation arranged such that when opposite sides of the wall contact one another on collapse of the wall, a continuous fluid passage is provided therebetween.

The wall is preferably of a liquid impermeable polymer. The surface formation may be in the form of a vertical channel on the inside of one or both sides of the wall. The valve preferably includes a valve member and a spring member that is arranged to urge the valve member outwardly to a sealing position, the valve member being pushed inwardly by engagement with the syringe against the action of the spring member to an open position. The valve and the syringe preferably have cooperating tapered surfaces which engage in a sealing manner when the syringe is inserted into the valve.

The container may include a seal across the valve that is ruptured on insertion of the syringe. The reservoir may contain a liquid drug.

A liquid transfer assembly including drug container, in accordance with the present invention, will now be described, by way of example, with reference to the accompanying drawings.

DETAILED DESCRIPTION

Figure 1:
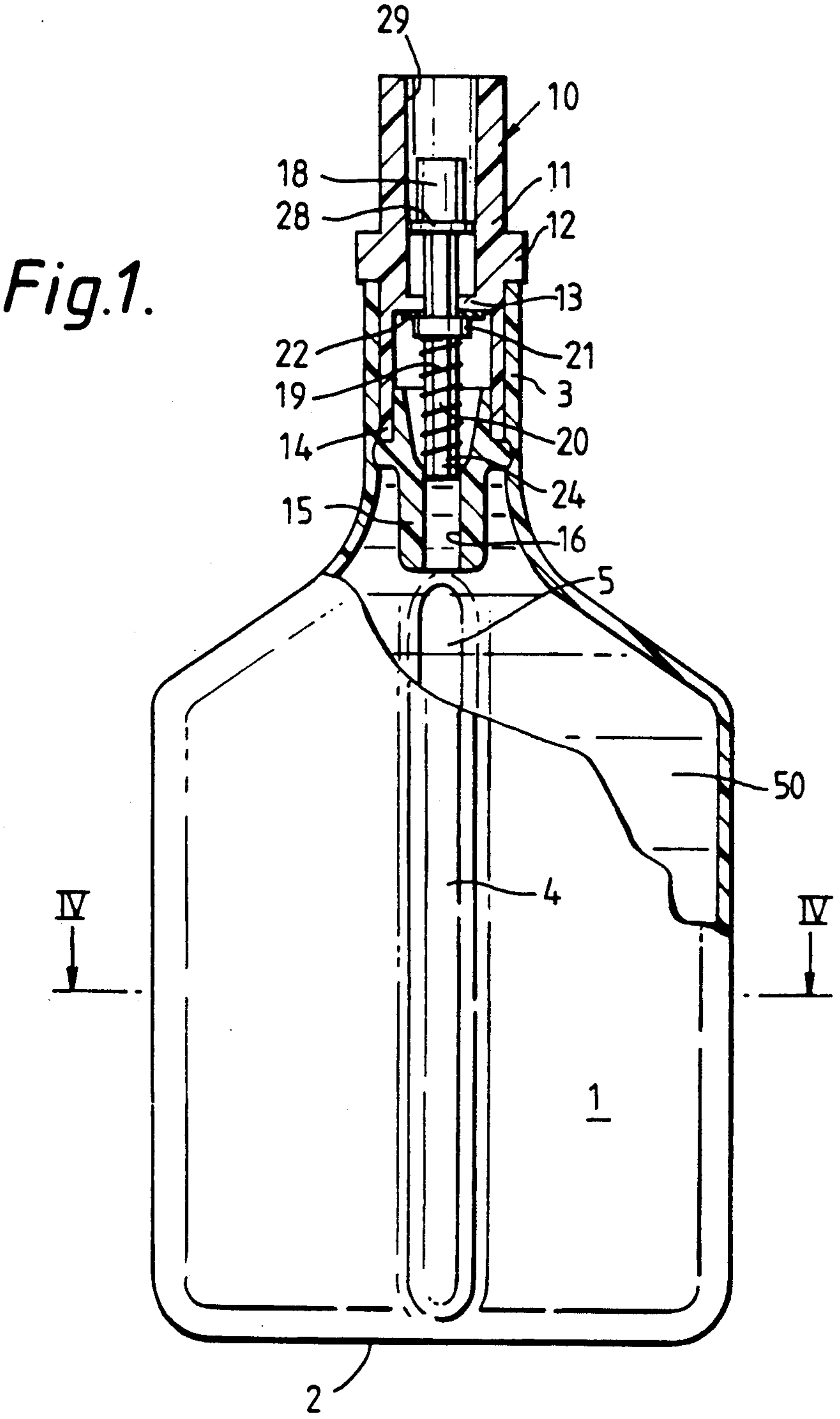
FIG. 1 is a partly sectional side elevation of the container in a closed state.
Figure 4:
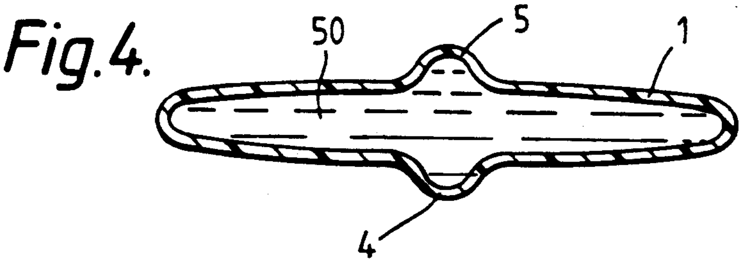
FIG. 4 is a transverse view along the line IV—IV of FIG. 1.

With reference first to FIGS. 1 and 4, the liquid transfer assembly comprises a drug container with a bag or reservoir 1 and a syringe 41. The reservoir 1 is made of a liquid impermeable polymer material such as PVC or a plastics laminate, the nature of the polymer material and the wall thickness of the bag 1 being such that the wall is flexible. The bag 1 is of oval section and, at its upper end, tapers to form a neck 3 of reduced diameter. The bag 1 is moulded with two opposite elongate vertical surface formations in the form of outwardly projecting spines 4 and 5 which form shallow vertical channels internally of the bag.

Within the neck 3 of the bag 1 there is sealed a valve assembly indicated by the numeral 10. The valve assembly 10 may be of conventional construction comprising an outer valve housing 11 of generally cylindrical shape and having an annular, outwardly-projecting shoulder 12 which engages the upper end of the neck 3. An integral flange 13 projects inwardly about half way along the length of the housing 11, the lower surface of the flange providing a valve seat of the valve. At the lower end 14 of the housing 11 there is mounted a tubular extension 15 having a bore 16 therethrough.

A movable valve member 18 is located in the housing 11 and is urged outwardly to the upper position shown in FIG. 1 by means of a helical spring 19. The spring 19 embraces the lower stem 20 of the valve member 18 and is trapped between the extension 15 and an annular shoulder 21 on the valve member. The shoulder 21 is located midway along the valve member 18 and supports on its upper surface a sealing washer 22 which engages the underside of the flange 13 on the housing when the valve member is in its natural, upper position.

Figure 3:
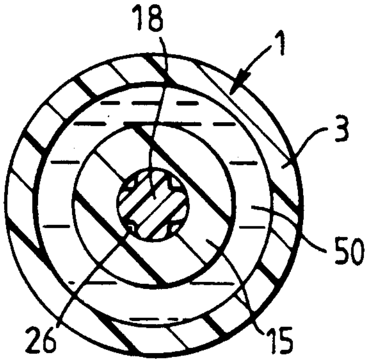
FIG. 3 is an enlarged transverse sectional view along the line III—III of FIG. 2.

The valve member 18 is a solid rod of plastics material and of substantially cylindrical shape. The lower end 24 of the valve member has a sliding fit within the bore 16 of the extension 15. The bore 16, or the lower part of the valve member 18, is shaped to permit liquid flow along the bore, around the outside of the valve member. In this respect, the valve member 18 may be provided with longitudinal grooves 26, as shown in FIG. 3. The upper end of the valve member 18 is similarly shaped or dimensioned where it passes through the aperture in the flange 13 so that liquid can flow between the flange 13 and the valve member when the sealing washer 22 is clear of the flange. The diameter of the upper end of the valve member 18 is smaller than that of the upper part of the valve housing 11 so that liquid is free to flow along the housing, between the housing and the valve member. A second annular shoulder 28 on the upper part of valve member 18 has a sliding fit within the upper part of the housing 11. The shoulder 28 is cut away with grooves or other apertures so that fluid is free to flow between the shoulder and the housing.

The bore 29 in the upper part of the housing 11 has a luer taper to fit the nose 40 of a syringe 41 (FIG. 2) inserted within the valve.

The container is filled with a drug, medicament or other liquid 50. In this respect the term 'liquid' is taken to cover powder suspensions in liquids, gels, pastes or the like which can be withdrawn by suction.

Before use, the valve 10 is in the state shown in FIG. 1, that is, with the valve member 18 in an upper position so that the spring 19 applies compression to the washer 22 between the shoulder 21 on the valve member and the flange 13 on the valve housing. This seals the valve closed preventing flow of air into the container and preventing escape of the contents.

Figure 2:
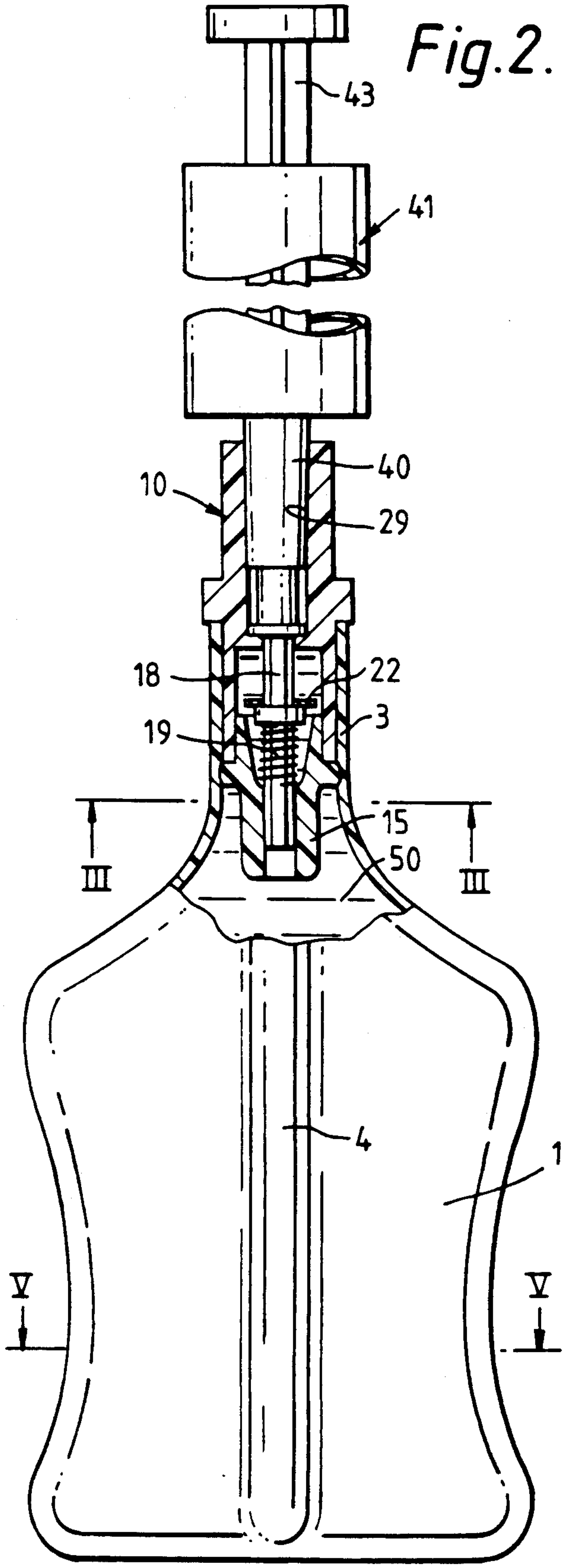
FIG. 2 is a partly sectional side elevation of the assembly during withdrawal of the contents of the container.

When it is desired to withdraw drug from the container, the nose 40 of the syringe 41 is pushed into the luer tapered bore 29 of the valve 10, in the manner shown in FIG. 2. The lower end of the nose 40 engages the top of the valve member 18 thereby pushing it down inwardly of the housing 11 against the action of the spring 19. As the nose 40 is pushed fully down it engages as a luer slip fit in the bore 29 to provide a fluid-tight seal with the valve and hence with the container. At the same time, the valve 10 is opened to allow communication between the syringe 41 and the interior of the bag 1.

Figure 5:
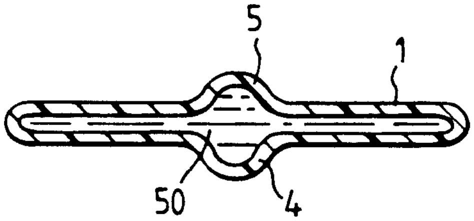
FIG. 5 is a transverse section view along the line V—V of FIG. 2.

The user then pulls the plunger 43 of the syringe 41 outwardly so that suction is applied and the drug 50 is drawn through the valve 10 into the syringe. As this happens, the walls of the bag 1 will collapse about its contents so that its internal volume is maintained substantially equal to the volume of liquid contents. This thereby avoids the need to vent the interior of the container which would allow air into contact with the contents. The vertical channels provided by the spines 4 and 5 ensure that fluid can be withdrawn from the bottom of the bag 1 even in a partially collapsed state, as shown in FIG. 5.

When the desired quantity of drug 50 has been withdrawn, the nose 40 of the syringe 41 is pulled out of the valve 10 thereby allowing the valve member 18 to rise and close the valve. The bag 1 is maintained in a collapsed or semi-collapsed state, without the admission of air.

A needle, not shown, can then be pushed onto the nose 40 of the syringe and the drug administered in the usual way.

Where the drug 50 has not been fully removed from the container, it is possible to remove further quantities at a later time.

By using a valve that can be opened by the nose of a syringe, the risk of injury by broken glass and needle pricks is removed. Disposal of used containers is also rendered safer. Wastage can be reduce because it may be possible to withdraw fluid from the container several times. The flexible nature of the bag makes it easier to pack and transport without damage. The risk of spillage from open containers is also reduced, and this is especially advantageous for cytotoxic drugs for chemotherapy.

The container of the present invention is also easier to handle, since the luer-taper fit of the syringe on the valve can be sufficient to retain the container on the syringe, leaving the user both hands free to hold the syringe barrel and plunger. The suction applied during withdrawal of the liquid further improves retention of the container on the syringe.

The withdrawl of drug from the container of the present invention can be achieved more quickly than from previous glass ampoules. Because air is evacuated from the container, there is reduced risk of air embolism from liquid administered by the syringe.

In place of the moulded spines 4 and 5, alternative surface formations could be provided on the interior of the bag to ensure that a vertical passage remains to the bottom of the bag when in a collapsed condition.

The use of a bag of plastics material readily enables it to be coloured so as to identify the nature of the contents, thereby reducing the risk of administration of incorrect drugs. The wall of the bag can be made opaque, if required, to reduce exposure of the contents to light.

A seal, rupturable by the syringe, may be applied across the top of the valve housing so that it is readily apparent whether or not the container has been used previously. This seal can also provide a visible guarantee of sterility.

It will be appreciated that the bag can be made of various other liquid-impermeable, flexible materials, such as metal foil, and that the bag can have different shapes. Other constructions of valve can also be used.

Where two liquids need to be mixed prior to transfer, they can be supplied in respective containers of the kind described above and coupled together by means of a double-ended male coupling piece. Each end of the coupling piece would open the valve in the respective container allowing liquid to be squeezed out of one container into the other and then back again. Repeated squeezing of the containers mixes their contents so that the mixed liquid can be transfered from either container, after removal of the coupling piece, by using a syringe as described as above.

What is claimed is:

1. A liquid transfer assembly for enabling the transfer of liquid from a container to a syringe comprising:

the syringe having a nose portion;

the liquid container comprising a reservoir and defining an opening therein;

a valve in said opening for selectively permitting the flow of liquid from said container to the syringe, said valve including means urging said valve to a normally closed position in which it blocks the flow of the liquid from the container to the syringe, said valve means further including means responsive to the forcible insertion of said nose portion of the syringe into said container opening to open said valve means to permit the flow of liquid from the container to the syringe, said valve having a tapered bore that forms a fit with the syringe inserted within said bore that is sufficient to retain said container on said syringe during normal use of the assembly;

a flexible wall for said container adapted to collapse about the contents of said container as the liquid is withdrawn therefrom thereby causing the internal volume of said container to be maintained substantially equal to the volume of the liquid remaining in the container, and at least one continuous, non-collapsible elongate channel extending longitudinally along substantially the full length of the interior side of at least one said flexible wall surface in the direction of flow of the liquid as it is emptied from said container in normal use thereof, said at least one channel being in communication over at least most of its length with the interior of said container to thereby maintain continuous liquid flow into said syringe as the opposite wall surfaces of the container collapse in response to the emptying of said container.

2. A liquid transfer assembly according to claim 1, wherein said wall is of liquid impermeable polymer.

3. A liquid transfer assembly according to claim 1, wherein said at least one channel is formed on the inside of both said wall channels.

4. A liquid transfer assembly according to claim 1, wherein the valve includes a valve member and a spring member, said spring member urging the valve member outwaraly to a sealing position, and wherein the valve member is pushed inwardly by engagement with said nose portion of said syringe against the action of the spring member to an open position.

5. A liquid transfer assembly according to claim 1, wherein the reservoir contains a liquid drug.

6. A liquid transfer assembly according to claim 1 in which said channels in said opposite wall surfaces oppose each other to form an enlarged channel between said wall surfaces.

7. A liquid transfer assembly for enabling the transfer of liquid drug to a syringe for subsequent injection comprising: a syringe, said syringe having a tapered nose, and a liquid drug container, said container comprising a reservoir for said drug, said reservoir having an opening thereto, a valve in said opening, said valve including a tapered bore, a valve member and a spring urging said valve member outwardly to a normally closed position to prevent liquid leaving the container, said valve member being pushed inwardly by engagement with the syringe against the action of the spring when the nose of the syringe is pushed into the bore of the valve to make sealing engagement with the bore, the fit of the syringe within said bore being sufficient to retain the container on the syringe, the reservoir having a wall of a flexible liquid impermeable polymer that is adapted to collapse about the contents of the container as liquid is withdrawn by the syringe such that the internal volume of the container is maintained substantially equal to the volume of liquid in the container, and the wall having opposite sides, each side having an internal surface provided with a respective channel, said channels being arranged such that when opposite sides of the wall contact one another on collapse of the wall a continuous fluid passage is provided therebetween.

* * * * *